(12) United States Patent
Fleming et al.

(10) Patent No.: US 7,491,488 B2
(45) Date of Patent: *Feb. 17, 2009

(54) METHODS, COMPOSITIONS, AND KITS FOR THE DETECTION OF BACTERIA IN A SAMPLE

(75) Inventors: James E. Fleming, Spokane, WA (US); Jason Buck Somes, Spokane, WA (US)

(73) Assignee: GenPrime, Inc., Spokane, WA (US)

( * ) Notice: Subject to any disclaimer, the term of this patent is extended or adjusted under 35 U.S.C. 154(b) by 21 days.

This patent is subject to a terminal disclaimer.

(21) Appl. No.: 11/149,979

(22) Filed: Jun. 9, 2005

(65) Prior Publication Data

US 2006/0014227 A1    Jan. 19, 2006

Related U.S. Application Data

(60) Provisional application No. 60/578,912, filed on Jun. 10, 2004.

(51) Int. Cl.
  *C12Q 1/00* (2006.01)
  *C12N 11/14* (2006.01)
  *C12M 1/00* (2006.01)

(52) U.S. Cl. .................. 435/4; 435/176; 435/287.1

(58) Field of Classification Search ............... None
See application file for complete search history.

(56) References Cited

U.S. PATENT DOCUMENTS

| | | | |
|---|---|---|---|
| 4,596,769 A * | 6/1986 | Shockman et al. | 435/7.32 |
| 4,888,279 A * | 12/1989 | Zeiger | 435/7.8 |
| 5,622,871 A | 4/1997 | May et al. | 436/514 |
| 6,184,027 B1 * | 2/2001 | Laine et al. | 435/261 |
| 6,352,862 B1 | 3/2002 | Davis et al. | 436/510 |
| 6,720,160 B2 * | 4/2004 | Wolde-Mariam | 435/7.32 |

OTHER PUBLICATIONS

Schrijver et al. Peptidoglycan From Sterile Human Spleen Induces T-Cell Proliferation and Inflammatory Mediators in Rheumatoid Arthritis Patients and Healthy Subjects; Rheumatology, vol. 40 (2001) pp. 438-446.*
Bendayan, M., Worth its Weight in Gold; Science, vol. 291, No. 5507 (2001) pp. 1363-1365.*
Chandler, J. et al., "The Place of Gold in Rapid Tests, IVD Technology," 2000, accessed Apr. 18, 2006, URL=http://www.devicelink.com/ivdt/archive/00/03/004.html, 10 pages.
Jones, K.D., "Troubleshooting Protein Binding in Nitrocellulose Membranes (Part I)—Principles, IVD Technology," 1999, accessed Apr. 18, 2006, http://www.devicelink.com/ivdt/archive/99/03/009.html, 10 pages.
Liu, C., et al., "Peptidoglycan Recognition Proteins: a Novel Family of Four Human Innate Immunity Pattern Recognition Molecules," *J. Biol. Chem.*, 276(37):34686-94, Sep. 14, 2001.
Liu, C., et al., "Mammalian Peptidoglycan Recognition Protein binds Peptidoglycan with High Affinity, is Expressed in Neutrophils, and Inhibits Bacterial Growth," *J. Biol. Chem.*, 275(32):24490-9, Aug. 11, 2000.
Monterrubio, I., "Rapid quality Testing Could Mean the Difference Between Selling Milk or Throwing it Away Before it Even Reaches the Consumer," *Food Quality*, pp. 40-41, Sep.-Oct. 2002.
Paek, S-H., et al., "Development of Rapid One-step Immunochromatographic Assay," *Methods*, 22(1):53-60, Sep. 2000.
Ravanis, S., et al., "Observations on the Effect of Raw Milk Quality on the Keeping Quality of Pasteurized Milk," *Lett Appl Microbiol.*, 20(3):164-7, Mar. 1995.
Sørhaug, T., et al., "Psychrotrophs and their Enzymes in Milk and Dairy Products: Quality Aspects," *Trends Food Sci. Technol.* 8:35-41, 1997.
Weiss, A.., "Concurrent Engineering for Lateral-flow Diagnostics, IVD Technology," 1999, accessed Apr. 18, 2006, URL=http://www.devicelink.com/ivdt/archive/99/11/009.html, 7 pages.

* cited by examiner

*Primary Examiner*—Jon P Weber
*Assistant Examiner*—Paul C. Martin
(74) *Attorney, Agent, or Firm*—Seed IP Law Group PLLC

(57) ABSTRACT

The present invention includes compositions, kits, and methods useful for the detection of bacteria. These agents and methods are primarily directed to a method of detecting the presence of bacteria in a sample, involving incubating the sample with an agent that binds to bacteria, such as, e.g., an agent specific for peptidoglycan or a component thereof, and then detecting bound bacteria. The invention includes lateral-flow immunoassay methods and devices for assessing the total bacterial load in a liquid sample.

10 Claims, 6 Drawing Sheets

Top View

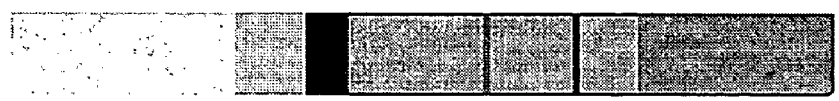

Side View

Sample wick
Sample pad
Conjugate pad

Nitrocellulose
Absorbent pad
Capture line

Control line

All pads and nitrocellulose are adhered to mylar backing.
Mouse anti-peptidoglycan antibody (IgG1) applied at capture line.
Goat anti-mouse IgG1 applied at control line.

Sample pad pretreated with blocking solution.

Conjugate pad pretreated with biotinylated mouse anti-peptidoglycan antibody and streptavidin-gold conjugate.

*FIG. 4*

METHODS, COMPOSITIONS, AND KITS FOR THE DETECTION OF BACTERIA IN A SAMPLE

CROSS-REFERENCE TO RELATED APPLICATION

This application claims the benefit under 35 U.S.C. § 119(e) of U.S. Provisional Patent Application No. 60/578,912 filed Jun. 10, 2004, wherein this provisional application is incorporated herein by reference in its entirety.

BACKGROUND OF THE INVENTION

1. Field of the Invention

The present invention relates to analytical methods of detecting the presence of bacteria in a sample. In particular, the invention relates to devices and methods suitable for the rapid detection of bacteria in a liquid sample, which may be used in a variety of settings, including homes, production facilities, clinics, laboratories, and the field.

2. Description of the Related Art

Bacterial contamination of water, beverages, food, pharmaceutical products, and other products ingested, used or excreted by humans or other animals is a relatively common source of infection and associated disease and is, consequently, a large concern for various food and drug manufacturers. Bacterial contamination is of particular concern to industries that produce and sell beverages, blood-related products, and pharmaceutical preparations, since these are directly introduced into the human or animal body. While the sources of bacterial contamination vary between industries, all industries attempt to minimize contamination and detect any contamination prior to the sale or use of the contaminated product.

Bacterial contamination is a continuing problem in the dairy industry (Ravanis and Lewis, *Lett. Appl. Microbiol.* 20:164-167, 1995). The Department of Agriculture has reported that over a billion pounds of milk are destroyed each year due to shelf-life expiration and microbial contamination (Monterubbio, *Food Quality*, September-October, pgs. 40-41, 2002). The occurrence of bacteria in raw milk typically comes from two sources, mastitis organisms in the udder and bacterial contamination of the teats from the environment (Reinemann et al, presented at the Annual Meeting of the National Mastitis Council, 1997). Procedures to reduce the bacterial load of raw milk have been dramatically improved in recent years; however, the problem of bacterial contamination still persists (Reinemann et al, supra).

Although standards vary from one dairy to another or from one state to another, all raw milk must be tested for its total bacterial content. The legal limit stated by the Pasteurized Milk Ordinance is 100,000 bacteria/ml for Grade A milk. Although this level of bacterial load is considered technically acceptable, most dairy processors strive for much more stringent standards. In many dairies, a standard of 10,000 bacteria/ml has been set and some set their standard at 1,000 bacteria/ml or 5,000 bacteria/ml. Every farm strives to maintain compliance with federal, state and local requirements (Reinemann et al, supra).

Raw milk is routinely tested by the standard plate count (SPC), which determines the number of colony forming units in a ml of milk following incubation at 32° C. for 48 hours. This test is almost always carried out in the dairy processor's laboratory or a contract laboratory and is rarely conducted at the farm level. Most dairies also carry out tests for coliforms, molds and total bacterial counts following incubation of the milk sample at 55° F. for 18 hours. This latter test provides information of the level of psychrotrophs in the sample (Sorhaug and Stepaniak, *Trends Food Sci. Technol.* 8:35-41, 1997). All of these tests are critical for determining the quality of raw milk prior to processing. Moreover, they have contributed significantly to improved milk quality, but they still suffer from the disadvantage of requiring long incubation times. Since SPCs take at least 24 hours to complete, raw milk is commingled from individual farms before the bacterial load has been established. Currently, truck drivers collect samples from multiple farms and transport them to the dairy for processing (Wetzel, Inland Northwest Dairy, Spokane, Wash., 2001, personal communication). By this time the milk is mixed and ready for processing.

A number of representatives from the milk industry have requested a rapid on-the-farm type screen that could assess the bacterial load of raw milk prior to its acceptance from the farm. This would be similar to the screening process for beta lactam antibiotics that is often conducted by the truck driver prior to receiving milk from a given farm. The dairy industry would benefit from the development of a rapid test that is inexpensive, easy to use and could be applied by farmers and truck drivers as well as dairy processors for rapidly assessing the microbial content of raw milk.

Another example of an industry faced with significant problems associated with bacterial contamination is the blood product industry. Bacterial contamination can occur in a variety of blood-based products used to treat humans, including, e.g., whole blood, red blood cells and platelets.

Bacterial contamination of platelets is of particular concern, since these organisms survive and readily multiply at temperatures of 20 to 24 degrees C., the storage temperature of platelets. Although the incidence of platelet contamination is greater from gram-positive organisms, fatalities due to platelet contamination tend to be equally divided between organisms that are gram-positive and gram-negative. The organisms most commonly implicated in fatalities, in descending order, are *Staphylococcus aureus, Klebsiella pneumoniae, Serratia marcescens*, and *Staphylococcus epidermidis*. Other isolated organisms include *Salmonella* sp., *Escherichia coli, Pseudomonas aeruginosa*, and *Bacillus cereus*. Skin contaminants, such as *Staphylococcus epidermidis* and *Bacillus* sp. are the organisms most implicated in platelet bacterial contamination. The seriousness of this problem is exacerbated by the fact that *Staphylococcus aureus* is the leading cause of nosocomial (hospital acquired) infections and is increasingly becoming resistant to conventional antibiotic therapies.

Bacterial contamination of transfusion products have been known as a potential source of harm since the beginning of transfusion history, but so far only a handful of countries actually test platelet products for contamination. In recent years, the focus has been directed towards viruses such as HIV and HCV, and new methods for detection have reduced the risk greatly. However, it is realized that the frequency of bacterial contamination of blood platelets and the incidence of illness and fatalities caused by bacterial contamination, greatly exceed that of viruses.

Detection of bacteria in platelets is difficult, mainly due to the very low initial inoculum present in the product. In addition, platelets may be contaminated with a range of bacteria that will grow at different rates. This makes sampling a major challenge to developers and users of test systems, and may cause the presence of bacteria in a product to be missed due to sampling error. Another challenge is the short shelf life of platelets (5-7 days). It is therefore very important to have a rapid and reliable method. Current methods may take days before a positive result is obtained, leaving very little shelf life for the products.

Methods, such as visual inspection or platelet swirling, although easy to implement, lack sensitivity resulting in an unacceptably high rate of false positives and the unnecessary destruction of viable and valuable platelets.

Metabolic methods, such as multi-agent indicator strips, which measure bacterial growth by decreases in glucose and pH levels, offer rapidity, but lack sensitivity, since several bacterial species have metabolic characteristics not responsive to these markers.

Traditional culture techniques require a lengthy incubation period of several days. False positives and false negatives may occur due to a variety of circumstances including the low number of bacteria present and incubation temperatures for a given organism. Automated bacterial culture tests, which are used in some European countries, have many of the same drawbacks found in the standard culturing techniques. They lack specificity for some types of platelet contaminating organisms and are unable to detect the presence of slow-growing bacteria.

Accordingly, there is a need in the art for methods and compositions for the rapid and sensitive detection of bacteria in liquid samples, including beverages and pharmaceutical preparations, such as milk, water, and blood products.

BRIEF SUMMARY OF THE INVENTION

In a first embodiment, the invention includes a device for the detection of bacteria, comprising a carrier to which a liquid sample suspected of containing bacteria can be applied, a binding agent that specifically binds bacteria, and a detection means. The device may further comprise a second binding agent that specifically binds bacteria. In one embodiment, a binding agent is immobilized in a first region of the carrier. In one embodiment, a binding agent binds peptidoglycan or a component thereof. In certain embodiments, a binding agent is labeled, while in other embodiments, it is not labeled.

In a related embodiment, the detection means is a label associated with a binding agent.

In one embodiment, the present invention provides a device for the detection of bacteria, comprising: a carrier to which a liquid sample suspected of containing bacteria can be applied; a labeled binding agent that is mobile in the carrier when in the moist state; and an unlabeled binding agent that is immobilized in a first region of the carrier. In a preferred embodiment, the binding agents bind peptidoglycan or a component thereof. The binding agents may be antibodies specific for peptidoglycan or a component thereof, such as N-acetylglucosamine, N-acetylmuramic acid, a tetrapeptide side chain of peptidoglycan, a peptide cross link of peptidoglycan or teichoic acid.

In a related embodiment, the carrier comprises: a liquid sample application wick; a conjugate pad comprising the labeled binding agent; a base pad comprising the unlabeled binding agent; a sample pad comprising a blocking agent; and an absorbent pad. The carrier may further comprise a control binding agent that is immobilized in a second region of the carrier and/or a detectable secondary agent that binds the labeled binding agent. In one embodiment, the labeled binding agent is labeled with biotin, and the detectable secondary agent comprises streptavidin. In a particular embodiment, the streptavidin is conjugated to colloidal gold.

In a related embodiment, the invention includes a method of detecting bacteria in a sample, comprising contacting a sample with a binding agent specific for peptidoglycan or a component thereof, and determining the presence of binding agent: bacteria complexes using a detection means. In certain embodiments, the binding agent is labeled. In one embodiment, the method further comprises contacting the binding agent: bacteria complexes with a second binding agent specific for peptidoglycan or a component thereof. In one embodiment, the detection means is associated with a binding agent. For example, the detection means may be a label attached to a binding agent.

In a related embodiment, the invention includes a kit for the detection of bacteria comprising a binding agent specific for peptidoglycan or a component thereof and a detection means. In one embodiment, the detection means is a label associated with a binding agent.

In yet another related embodiment, the invention provides a kit for the detection of bacteria, comprising: a labeled binding agent that specifically binds peptidoglycan or a component thereof; an unlabeled binding agent that specifically binds peptidoglycan or a component thereof; and a carrier to which a liquid sample may be applied. The kit may also include a detectable secondary agent that binds the labeled binding agent. In certain embodiments, the labeled binding agents are antibodies such as monoclonal or polyclonal antibodies or fragments thereof. In one embodiment, the labeled binding agent is labeled with biotin. In a related embodiment, the secondary agent comprises streptavidin, which may be conjugated to colloidal gold.

In another embodiment, the invention provides a method of detecting bacteria in a sample, comprising: incubating a sample with a binding agent that binds peptidoglycan or a component thereof; and detecting binding agent bound to the sample, thereby detecting bacteria in the sample. In one embodiment, the binding agent is labeled. In another embodiment, the binding agent is not labeled. In certain embodiments, the binding agents are antibodies such as monoclonal or polyclonal antibodies or fragments thereof. In certain embodiments, the sample is a liquid. The sample may be a beverage such as milk, soy milk, water, beer, wine, juice, cider, or carbonated beverages. In related embodiments, the label is biotin, latex, colloidal gold, fluorescent dye, or an enzyme. In other embodiments, the sample comprises biological material. In one particular embodiment, the biological material is obtained from a wound site. In related embodiments, the biological material is tissue or biological fluid.

An additional embodiment of the invention provides an analytical test device for detecting the presence of bacteria in a liquid sample, comprising: a hollow casing having a liquid sample application aperture and a means permitting observation of a test result; and a carrier comprising a dry porous material contained within said hollow casing, said carrier communicating directly or indirectly with the exterior of said hollow casing through said liquid sample application aperture to receive applied liquid sample, said carrier having a test result zone or capture line observable via said means permitting observation, said carrier, in the dry unused state, containing a labeled agent capable of specifically binding bacteria to form a first complex of said labeled agent and said bacteria, wherein said labeled agent is dry on said carrier prior to use and is released into mobile by said applied liquid sample, and said carrier containing in said test result zone or capture line a means for specifically binding said first complex, said means for binding being immobilized in said test result zone; wherein said binding means binds said first complex to form a second complex, said second complex being observable via said means permitting observation, thereby to indicate the presence of bacteria in said liquid sample. In particular embodiments of the device, the dry porous material is nitrocellulose or nylon.

In a related embodiment, the device also includes a control zone or control line downstream from said test result zone or capture line in said carrier to indicate that said liquid sample is conveyed beyond said capture line, and a control line observation aperture in said casing, said control line also being observable from outside said hollow casing through said control line observation aperture. In one embodiment, the control line contains a means for binding said labeled agent and wherein said means is immobilized in said control line. In one embodiment, said means comprises an antibody or fragment thereof that specifically binds any portion of said labeled agent. The antibody may, in certain embodiments, be a monoclonal or polyclonal antibody or fragment thereof, such as an $F_c$, $F_a$, $F_b$, and $F_a + F_b$ region of an antibody.

BRIEF DESCRIPTION OF THE SEVERAL VIEWS OF THE DRAWING(S)

FIG. 1 is a photograph showing the results of an indirect enzyme-linked immunosorbent assay (ELISA) using mouse monoclonal anti-peptidoglycan to detect bacteria. Wells were coated with ten-fold dilutions of bacteria suspended in PBS, 100 ul per well. Columns, from left to right, received undiluted suspension through $10^{-8}$ with the final column receiving sterile filtered PBS. Rows, from top to bottom, received twofold dilutions of mouse anti-peptidoglycan beginning with 100 ug/ml and ending with 1.56 ug/ml, 50 ul per well. The bottom row received sterile filtered PBS, also 50 ul per well. The plate on the left was coated with *E. coli* and the plate on the right with a *Lactobacillus* spp.

FIG. 2 shows graphs representing data from ELISA using monoclonal anti-peptidoglycan (PG) antibody and *E. coli* (FIG. 2*a*) and *Lactobacillus* sp. (FIG. 2*b*). The ELISA format known as a checkerboard titration was used for each type of bacteria. The color change was measured with a microtiter plate reader by recording the absorbance of each well at 405 nm.

FIG. 4 is a diagram showing the layout of one embodiment of a capture antibody device used to determine the presence of total bacteria in raw milk.

Figure 6:
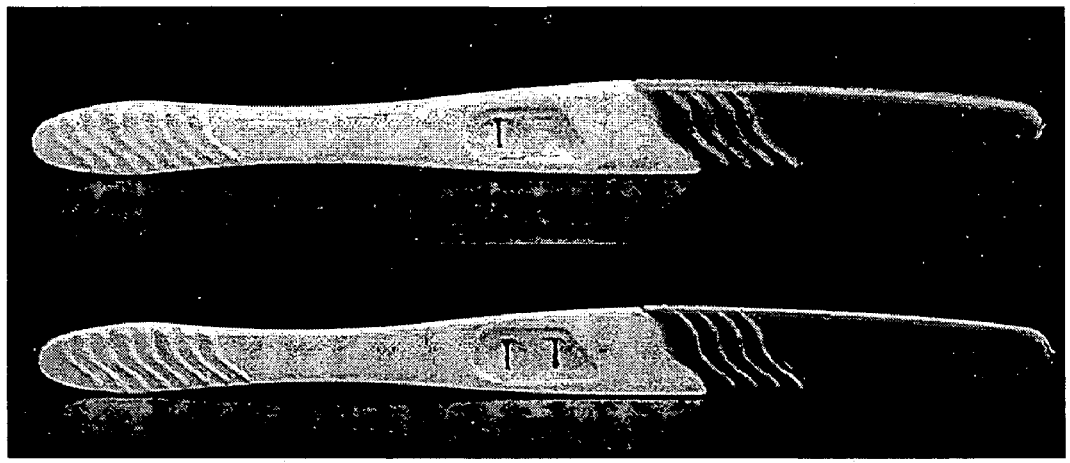

FIG. 6 is a photograph demonstrating negative and positive test results. The round window to the left is the control window and the square window to the right is the test window. The presence of one line indicates a negative test (top). The presence of two lines indicates a positive test (bottom).

DETAILED DESCRIPTION OF THE INVENTION

The present invention is directed to novel methods and devices useful for the detection of bacteria. The invention is based, in part, upon the discovery that binding agents specific for bacteria may be used to rapidly and sensitively detect the presence of bacteria in a liquid sample. Although the skilled artisan would appreciate that the invention includes a variety of embodiments, one particular embodiment of the invention uses antibodies against peptidoglycan, or one or more components thereof, to detect both gram positive and gram negative bacteria in liquid samples. Furthermore, while the invention may be practiced by a variety of methods available in the art, in one embodiment, the invention is directed to methods and devices for lateral flow immunological detection of bacteria in a liquid sample. Accordingly, the invention provides novel, rapid, and reliable methods and devices suitable for detecting the presence of bacteria in a variety of liquid sample, including, e.g., milk, water, and blood-related products, such as platelets.

A. Methods of Detection

In one aspect, the invention provides novel methods of detecting the presence of bacteria in a sample. In certain embodiments, the invention includes methods of determining whether a threshold level of bacteria is present in a sample. In other embodiments, the invention may be used to estimate or quantify the amount of bacteria present in a sample.

At a fundamental level, the invention involves combining a sample to be tested for the presence of bacteria with an agent that binds bacteria, and then determining whether any complexes containing both the binding agent and bacteria are present. Accordingly, in one embodiment, the invention includes a method of detecting bacteria in a sample, comprising incubating a sample with a binding agent that binds bacteria and detecting binding agent bound to the sample, thereby detecting bacteria in the sample. In one embodiment, the binding agent binds peptidoglycan or a component thereof.

In certain embodiments, the binding agent is labeled or comprises a label that is detectable either directly or indirectly. In other related embodiments, the microorganism being detected is labeled, for example, by metabolic labeling using a radiolabeled compounds, such as, e.g., $^3$H, $[^{35}S]$-methionine or $[^{35}S]$-cysteine. In certain embodiments, the label is detectable visually or using an appropriate instrument. One of skill in the art would appreciate that the instrument used will depend, in large part, upon the label or complex being detected and is apprised as to the selection of an appropriate instrument suitable for any label available in the art and used according to the present invention. Examples of such instruments include, but are not limited to: light sources, spectrophotometers, and fluorometers. Further examples of specific instruments include, but are not limited to, the RAMP fluorescent reader (Response Biomedical, Burnaby, BC, Canada), the SPECTRAMAX® M2, LmaxII luminescence micro plate reader, Gemini XPS fluorescence micro plate reader, and the Versamax absorbance micro plate reader (Molecular Devices Corporation, Sunnyvale, Calif.).

Generally, the presence of bacteria in the sample being analyzed is determined by comparing the amount of label detected in the sample to a control amount. The control amount may be a predetermined value, or, alternatively, the control amount may be the amount of label detected in a control sample, such as, e.g., a sample known to not contain bacteria or samples known to contain a specific amount or concentration of bacteria. In one embodiment, the presence of a significant amount of bacteria is determined by comparing the amount detected to a threshold level. The threshold level may be any level suitable in the industry or for a particular type of sample or bacteria and, therefore, may be based on industry or other regulatory standards. The skilled artisan will appreciate that threshold levels may be readily determined based upon such criteria and routine procedures. In one embodiment, the label is only detectable, e.g., visually, when the amount of bacteria in a sample meets or exceeds a particular threshold level. In a further embodiment, bacteria is detected in a sample if the value of detected label is at least two-fold, three-fold, or five-fold greater than the amount detected in a negative control that does not contain bacteria. In certain embodiments, an amount of bacteria detected is determined by comparing the amount of label detected to standard values correlated with particular amounts or concentrations of bacteria and extrapolating to establish the amount of bacteria in the sample tested.

The present invention may be practiced using one or more binding agents. In one embodiment, the invention utilizes two binding agents, which may be the same or different. In certain embodiments, one binding agent is referred to herein as the detection binding agent, since the methods of the invention involve detecting complexes of bacteria and this binding agent. This binding agent may be labeled or not labeled. A second binding agent that may be used according to certain embodiments of the invention is referred to herein as the capture binding agent. Generally, the capture binding agent is immobilized on a support, so when it is bound to bacteria or complexes of bacteria and detection binding agent, the bacteria or complexes are retained at the region of the support where the capture binding agent is immobilized. In certain embodiments, the capture binding agent and the detection binding agent are the same molecule.

In certain embodiments, the capture binding agent is immobilized on a support, a sample is introduced to the immobilized binding agent, and the presence of bacteria bound to the immobilized binding agent is determined, typically using a detection binding agent that also binds to the bacteria. In one embodiment, the detection binding agent comprises a label that facilitates detection of complexes of bacteria and detection binding agent. In another embodiment, the bacteria itself is labeled, and the detection binding agent need not be labeled. It should be noted that, for all methods of the invention, the sample may be combined with the capture binding agent before, after, or simultaneously with the detection binding reagent. Accordingly, in different embodiments, the capture binding agent may bind bacteria alone or may bind bacteria bound to the detection binding agent.

It is understood, however, that the capture binding agent may be labeled. In one embodiment, if the capture binding agent is labeled, the label will be different than the label of the detection binding agent. In one example, one or both of the binding agents contain labels suitable for fluorescence resonance energy transfer (FRET) detection of a complex containing both binding agents. FRET labels and methods are widely available and known in the art.

In certain embodiments, the capture binding agent may be labeled such that a signal is detectable upon binding of the bacteria-associated molecule to the capture binding agent. Accordingly, labeled binding agents include binding agents that undergo a change upon binding, such that the agent emits a detectable signal. Additionally, the invention contemplates a variety of other detection means, including, e.g., the use of biosensors, such as those described, e.g., in U.S. Pat. Nos. 6,540,890, 6,503,381, and 6,547,954 and references described therein.

The basic method of the invention may be practiced in several different permutations, depending, in part, upon whether the capture binding agent, detection binding agent, or bacteria is labeled, or whether a labeled secondary agent is used to determine the presence of complexes comprising the bacteria and detection binding agent. For example, in one embodiment, the method of the invention involves contacting a bacteria with a labeled detection binding agent, and detecting complexes of bacteria and labeled detection binding agent using a capture binding agent. Another embodiment of the method of the invention involves metabolically labeling a bacteria, contacting the labeled bacteria with a detection binding agent, e.g., an antibody to peptidoglycan or a component thereof, and detecting complexes of labeled bacteria and detection binding agent using a capture binding agent. In yet another embodiment, the method involves contacting a bacteria with a detection binding agent and a labeled secondary agent that binds to the detection binding agent, and detecting complexes of bacteria, detection binding agent and labeled secondary agent using a capture binding agent. In yet another related embodiment, the method includes contacting a complex of the complex of labeled bacteria and bound detection agent with a secondary binding agent, e.g., an antibody that binds to the detection binding agent. While these aspects of methods of the invention are describe for exemplary purposes, the invention includes any and all variations of the methods described herein.

The methods of the invention may be practiced using a variety of known techniques, depending, in part, upon the nature of the binding reagents. For example, the capture binding reagent may be immobilized in a column, and the sample may be passed through the column. In other embodiments, the invention may be practiced by various immunological assays, including immunosorbent assays such as, e.g., enzyme-linked immunosorbent assays (ELISAs) using antibodies specific for bacteria. In one embodiment, the methods employ "sandwich" assays wherein the bacteria is bound by a first binding agent and then detected by a second binding agent, which may be the same or different from the first binding agent. A wide variety of various binding assays are well-known in the art, and the skilled artisan would readily understand how to adapt such assays according to the present invention.

In one embodiment, methods of the invention are practiced using lateral flow techniques, including, e.g., lateral flow methods described in U.S. Pat. Nos. 5,622,871 and 6,352,862, and references and patents cited within. According to one embodiment of the invention, methods using lateral flow techniques involve applying a liquid sample to one edge of a carrier comprising a porous material through which the sample can flow. A capture binding agent is immobilized in a region of the carrier (the capture line), such that when the sample flows over or through the capture line, bacteria present in the sample bind to the capture binding agent and are retained at the capture line. In certain embodiments, detection binding agent is also present on the carrier, but it is mobile when wet by the liquid sample or bound to bacteria present in the liquid sample. Accordingly, as a liquid sample flows through the carrier, it comes into contact with both the capture binding agent and the detection binding agent, resulting in the formation of a tertiary complex including detection binding agent, bacteria, and capture binding agent at the capture line on the carrier.

In embodiments using a labeled detection binding agent or labeled microorganism, the presence of the complex is then determined via the label present in the detection binding agent or microorganism, either directly, or indirectly using a secondary agent that interacts with the label to produce a detectable signal. One example of potential secondary agents useful accordingly to the invention are labeled secondary antibodies, such as, e.g., gold- or fluorescently-labeled goat anti-mouse or goat anti-rabbit antibodies, that specifically bind to antibodies or fragments thereof. A variety of such secondary antibodies are known and available in the art, and any may be used according to the present invention. Typically, the signal generated by the label or detection agent is visually detectable or may be detected using any instrument or means available in the art, including, but not limited to, a light source, a spectrophotometer, or a fluorometer. A diagram of one specific embodiment of the method of the invention is provided in FIG. 3, and further details of specific embodiments of lateral flow methods and devices are provided infra.

1. Samples

The invention may be used to detect the presence of microorganisms, including, e.g., bacteria in a variety of samples. While the invention is typically used to detect bacteria in liquid samples, it may also be used to detect bacteria in solid samples that are suspended or dissolved in a liquid. Alternatively, a solid sample may be soaked in a liquid to release bacteria from the sample into the liquid, and the liquid may then be tested for the presence of bacteria. In certain embodiments, a liquid sample may be diluted before being tested, e.g., in water or a buffer such as phosphate buffered saline (PBS). The invention has wide applications, since it should be able to detect a threshold bacterial load in any liquid sample. Examples of liquid or solid samples include, but are not limited to: urine, cerebral spinal fluid, saliva, amniotic fluid, vaginal fluid, semen, platelets, blood products, myocardial fluid, stomach acid/secretions, juices, milk and milk products, breast milk, soy milk, beer, wine, canned foods, processed foods, liquid foods, well water, dental water unit lines, RV water tanks, airplane water tanks, refrigerator water lines, fish tanks, animal water, cosmetics, yogurt, liquified meat products, baby food, formula, apple or other cider, sterilized lab reagents, petroleum products, non-autoclavable lab reagents, feces, and waste water.

In certain embodiments, the invention may be used to detect the presence of bacteria in a beverage or food. Beverages that may be tested according to the invention include, but are not limited to, milk products, e.g., milk and cream; alcoholic beverages, e.g. beer and wine; juices, formula, liquid foods, and water. Such products may be tested at any stage in their production. For example, milk may be tested immediately after or shortly after being obtained from the animal or following further processing, such as pasteurization. Wine for example, may be tested while it is still grape juice, at different stages of fermentation, or following sedimentation or filtration. Water that may be tested includes, but is not limited to, drinking or potable water. Water from any source may be tested according to the invention, including, e.g., water from swimming pools, heating and cooling systems, and natural or outdoor waters, e.g., lakes and rivers. A variety of food products may also be tested, although depending upon the nature and consistency of the food product, it may need to be further processed prior to test, for example, by diluting or dissolving the food in a liquid. One example of a food product that might be tested according to the invention is yogurt. Another example is baby foods.

In other embodiments, the invention may be used to detect the presence of bacteria in blood products and pharmaceutical preparations. For example, the invention may be used to detect bacteria in preparations comprising whole blood, platelets, red blood cells, or leukocytes, including concentrates suitable for transfusion.

2. Bacteria

The present invention may be used to detect the presence of a variety of bacteria, including aerobic and anaerobic bacteria and gram positive and gram negative bacteria. In certain embodiments, the invention may be used to detect bacteria associated with bacterial contamination of beverages and foods and/or infection of humans or other animals.

In certain embodiments, the invention is used to detect the presence of aerobic or anaerobic bacteria in blood or blood products. Examples of aerobic bacteria associated with blood infections and related disease include, amongst others, *Neisseria, Pseudomonas aeruginosa, Staphylococcus aureus, Klebsiella pneumoniae, Serratia marcescens*, and *Staphylococcus epidermidis*. Other organisms that may be detected include, e.g., *Salmonella* sp., *Escherichia coli, Pseudomonas aeruginosa*, and *Bacillus cereus*. Examples of anaerobic bacteria that may cause infections of the blood include, but are not limited to, *Bacteroides, E. coli, Klebsiella*, and *Clostridium*. It is further understood that detection can be accomplished independent of the genus or species; thus, any organism that contains peptidoglycan or a component of peptidoglycan may be detected according to the invention.

In other embodiments, the invention is used to detect the presence of gram positive or gram negative bacteria, including pathogenic bacteria, in beverages or food products. In some cases, milk can contain pathogenic bacteria, such as *E. coli, salmonella*, and *listeria*. For example, research conducted by the British government recently found contamination with a form of tuberculosis bacterium in about 10% of samples of milk. The bacterium, *mycobacterium avium paratuberculosis* (MAP), has been linked to Crohn's disease in humans.

Examples of other bacteria that may be detected include, but are not limited to, the gram-negative strains: *Spirochaeta* sp, *Cristispira* sp, *Treponema* sp, *Borrelia* sp, *Leptospira* sp, *Campylobacter* sp, *Spirillium* sp, *Spirosoma* sp, *Pseudomonas* sp, *Xanthomonas* sp, *Phisobium* sp, *Methylococcus* sp, *Halobacterium* sp, *Acetobacter* sp, *Legionella* sp, *Neisseria* sp, *Moraxella* sp, *Flavobacterium* sp, *Brucella* sp, *Bordetrella* sp, *Francisella* sp, *Escherichia* sp, *Shigella* sp, *Salmonella* sp, *Citrobacter* sp, *Klebsiella* sp, *Enterobacter* sp, *Erwinia* sp, *Serratia* sp, *Hafnia* sp, *Edwardsiella* sp, *Proteus* sp, *Providencia* sp, *Morganella* sp, *Yersina* sp, *Vibrio* sp, *Pasterurella* sp, *Haemophilus* sp, *Desulfuromanas* sp, *Desulfovibrio* sp, *Desulfomanonas* sp, *Desulfococcus* sp, *Desulfobacter* sp, *Desulfobulbus* sp, *Desulfosarcina* sp, *Veillonella* sp, *Rickettsia* sp, *Rochalimeae* sp, *Coxiella* sp, *Ehrlichia* sp, *Cowdria* sp, *Wolbachia* sp, *Rickettsiella* sp, *Chlamydia* sp, *Mycoplasma* sp, *Ureaplasma* sp, and *Spiroplasma* sp.

Examples of gram-positive bacteria that may be detected include, but are not limited to: *Micrococcus* sp, *Stomatococcus* sp, *Planococcus* sp, *Staphlycoccus* sp, *Deinococcus* sp, *Streptococcus* sp, *Sarcina* sp, *Pediococcus* sp, *Bacillus* sp, *Sporolactobacillus* sp, *Clostridium* sp, *Desulfotomaculum, Sporosarcina* sp, *Gardnerella* sp, *Streptobacillus* sp, *Lactobacillus* sp, *Listeria* sp, *Erysipelothrix* sp, *Corynebacterium* sp, *Mycobacterium* sp, *Nocardia* sp, *Haemophillus* sp, and *Heliobacter* sp.

Typically, the invention contemplates the detection of a threshold level of bacteria in a sample. The skilled artisan would readily appreciate that the relevant threshold level depends, in large part, upon the sample being tested, the type of bacteria suspected of being present in the sample, and any industry or government-imposed standards related to maximum bacterial concentration. The determination of an appropriate threshold level for a particular sample to be tested may readily be determined by the skilled artisan based upon these and any other criteria established for a suitable application. Accordingly, the methods and devices of the invention may be optimized and/or the sensitivity adjusted such that a positive indication of the presence of bacteria in a sample occurs only when the amount of bacteria is above a certain threshold level. The sensitivity of the methods and devices of the invention may be adjusted by a variety of means well understood in the art, including, for example, by varying the concentration of one or more of the following components that may be present in the system: capture binding agent, secondary or labeled binding agent, and detection agent. In certain embodiments, the threshold level is $1\times10^2$ organisms/ml, $5\times10^2$ organisms/ml, $1\times10^3$ organisms/ml, $2\times10^3$ organisms/ml, $5\times10^3$ organisms/ml, $1\times10^4$ organisms/ml, $2\times10^4$ organisms/ml, $5\times10^4$ organisms/ml, $1\times10^5$ organisms/ml, or $5\times10^5$ organisms/ml, or any integer value falling between. The threshold level may, alternatively be expressed as the number of colony forming units (cfu) present in a sample, and the threshold level may be, e.g., 50 cfu/ml, $1\times10^2$ cfu/ml, $5\times10^2$ cfu/ml, $1\times10^3$ cfu/ml, $2\times10^3$ cfu/ml, $5\times10^3$ cfu/ml, $1\times10^4$ cfu/ml, $2\times10^4$ cfu/ml, $5\times10^4$ cfu/ml, or $1\times10^5$ cfu/ml, or any integer value falling between. Examples of suitable threshold levels for certain different samples include: milk: $5\times10^3$ cfu/mL to $1\times10^5$ cfu/mL, water: 10 cfu/mL to $1\times10^5$ cfu/mL, blood: 10 cfu/mL to $1\times10^6$ cfu/mL, urine: 10 cfu/mL to $1\times10^6$ cfu/mL, and beer: 10 cfu/mL to $1\times10^7$ cfu/mL.

3. Binding Agents

The detection system of the invention is based, in large part, on the ability of an agent to bind bacteria. Generally, the invention contemplates the use of a binding agent that specifically binds bacteria, resulting in the formation of a detectable complex of bacteria and binding agent. In one embodiment, the invention utilizes two binding agents, a capture binding agent and a detection binding agent, both of which bind to bacteria, resulting in the formation of a ternary complex comprising capture binding agent, bacteria, and detection binding agent. Any of a variety of binding agents may be used, including, for example, polypeptides, sugars, and nucleic acids. In yet another embodiment, the invention further includes the use of an additional binding agent that binds to the detection binding agent. Such an additional binding agent may be useful, e.g. in detecting bound detection binding agent. Accordingly, one example of such an additional binding agent is antibodies specific for a fragment of an antibody, e.g., an $F_c$ fragment, which may be detectably labeled and, therefore used to detect bound detection binding agent, and are particularly useful when the detection binding agent is not itself easily amenable to labeling.

One example of a binding agent is peptidoglycan recognition proteins (PGRPs). Without wishing to be bound by theory, it is believed that PGRPs are components of the innate immune system that recognize microorganisms through a series of pattern recognition receptors that are highly conserved in evolution. PGRPs have been identified in a variety of organisms, including, e.g., insect and mammals. PGRP's recognize peptidoglycan, a ubiquitous component of bacterial cell walls. Insects have a family of at least 12 peptidoglycan recognition proteins (PGRPs) and at least four human PGRPs (PGRP-L, PGRP-Iα, PGRP-Iβ, and PGRP-S) have been identified. PGRPs are described, e.g., in Liu, C. et al., *J. Biol. Chem.*, 276: 34686-34694, 2001. PGRPs specifically bind peptidoglycan, and it has been shown that mouse PGRP binds peptidoglycan with nanomolar affinity (Liu, C., et al., *J. Biol. Chem.* 275:24490-24499, 2000). *Drosophila* PGRPs may be generally grouped into two classes: short PGRPs (PGRP-S), which are small extracellular proteins, and long PGRPs (PGRP-L), which have long transcripts and are either intracellular or membrane-spanning proteins.

In certain embodiments, the binding agent is an antibody specific for bacteria. In one embodiment, the binding agent specifically binds to the cell surface of bacteria. The binding agent or antibody may be specific for one or more different types or strains of bacteria. In certain embodiments, the binding agent binds to gram-positive or gram-negative bacteria or both. Alternatively, and in an embodiment preferred for the detection of unknown bacteria or for detecting all or most types of bacteria, the binding agent or antibody recognizes all or a large number of different bacteria. In certain embodiments, an antibody binding agent is a monoclonal antibody, a polyclonal antibody, or a fragment thereof. Antibody fragments include all capable of binding to a bacteria, including, e.g., $F_c$, $F_a$, $F_b$, and $F_a+F_b$ regions of an antibody. Furthermore, the capture binding agent and detection binding agent may comprise the same binding moiety, and the detection binding agent and/or capture binding agent may further include a label or other detection means. In certain embodiments, one or both of the two binding agents is directed against a component of the bacterial surface. In one embodiment, a binding agent is an antibody, e.g., monoclonal antibody, that binds peptidoglycan or a components thereof, such as, e.g., N-acetyl-glucosamine (NAG) and N-acetyl-muramic acid, a tetrapeptide side chain of peptidoglycan, a peptide crosslink of peptidoglycan, or teichoic acid. In a further embodiment, the binding antibody binds to whole peptidoglycan. Other examples of binding targets include, but are not limited to, glucosamine, peptidoglycan, NAG (N-acetylglucosamine), NAM (N-acetylmuramic acid), MDP (muramyl dipeptide), muropeptides, muramic acid, and muramic lactam (spores).

As used herein, an antibody or binding agent is said to be "immunospecific" or to "specifically bind" bacteria or a molecule or component thereof if it reacts at a detectable level with bacteria or a molecule or component thereof, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci.* USA 51:660 (1949)) or by surface plasmon resonance (BIAcore, Biosensor, Piscataway, N.J.). See, e.g., Wolff et al., *Cancer Res.* 53:2560-2565 (1993).

4. Detection Means

According to the invention, detection of bacteria in a sample is accomplished through the use of a detection means. Generally, the detection means is associated with either the detection binding agent or the capture binding agent. Any suitable means known in the art may be employed. In one embodiment, any detection means capable of producing, either directly or indirectly, a detectable signal upon binding of a binding agent to bacteria may be used. The detection means may facilitate detection directed or indirectly, e.g., through the use of a secondary agent.

In certain embodiments, the detection means is a label. The presence of the label may be detected by a variety of different methods, depending upon the nature of the label used. Accordingly, in certain preferred embodiments, the label may be detected visually. Examples of labels include, but are not limited to, biotin, latex, colloidal gold, fluorescent dyes, radiolabels, and enzymes.

In certain embodiments, the label is a particulate label. A variety of such "direct labels" are known in the art, including, e.g., colored latex particles, gold sols, non-metallic colloids, and dye sols. Such labels can be used to produce an instant analytical result without the need for additional reagents to develop a detectable signal. They are robust and stable and can, therefore, be used readily in an analytical device that is stored in the dry state. Their release upon contact with a liquid sample can be modulated, for example, by the use of soluble glazes.

In one embodiment, a particulate label is a latex label, such as a colored latex label that can be readily visible to the eye if it becomes bound at the detection zone.

In certain embodiments, a label may be a fluorescent compound, which can respond to applied electromagnetic energy, such as ultraviolet or visible light, to provide an emitted signal that can be detected visually or detected instrumentally.

In certain embodiments, "indirect labels" may be used according to the invention. Such labels usually require the addition of one or more secondary or developing agents such as substrates before a visible signal is detectable. These agents include, amongst others, enzymes such as horseradish peroxidase and alkaline phosphatase.

In one embodiment, the label is horseradish peroxidase, and the secondary agent is ABTS, which reacts with horseradish peroxidase to produce a colored reaction that may be detected visually or by measuring absorbance using an appropriate filter, typically at 405 nm.

In another embodiment, the label is biotin, and the secondary agent comprises streptavidin. In one embodiment, the secondary agent is a streptavidin-gold conjugate.

Coupling of a label to a binding agent to produce a labeled binding agent may be performed by a variety of methods known in the art, including covalent bonding or by hydrophobic bonding. In one embodiment, an antibody may be labeled, e.g., using the BiotinTag Micro-biotinylation Kit from Sigma Chemical Co, St. Louis, Mo.

In embodiments wherein the invention is used to identify the presence of more than one analyte in a sample, the several different labeled binding agents may be used, each carrying a different label.

B. Detection Devices

The invention further provides apparatuses, devices and kits that may be employed according to methods of the invention to detect bacteria. A variety of related devices have been described generally, particularly for methods of detecting pregnancy, and are described, e.g., in U.S. Pat. Nos. 5,622,871 and 6,352,862, and references and patents cited therein; Jones, K. D. (1999) Troubleshooting Protein Binding in Nitrocellulose Membranes (Part I)—Principles, IVD Technology; Chandler, J. et al. (2000) The Place of Gold in Rapid Tests, IVD Technology; Weiss, A. (1999) Concurrent Engineering for Lateral-flow Diagnostics, IVD Technology; and Paek, S. et al. (2000) Development of Rapid One-step Immunochromatographic Assay, Immun. Methods, 22:53-60. The devices of the invention and kits comprising the same may be readily prepared using known methods, including those described in the aforementioned references. In certain embodiments, these devices are prepared so that they may be stored in a dry form to facilitate stability and increase shelf-life.

While the components of devices and kits of the invention will necessarily vary depending upon the particular method of detection being used, such devices and kits will generally include a carrier containing a capture line (i.e., detection zone), a capture binding agent, and a detection binding agent. Typically, the capture binding agent will be present on the carrier. In certain embodiments, the detection binding agent may also be present on the carrier, or it may be separate from the carrier.

The carrier refers generally to the physical medium upon which the methods of the invention are practiced. The carrier is preferably a porous carrier material in the form of a strip or sheet to which during manufacture of the device, one or more reagents or physical components can be applied in spatially distinct zones. The carrier may comprise a single physical component, but usually the carrier will comprise multiple different physical components, including any of, e.g., a sample wick, a sample pad, a conjugate pad, a capture line, a control line, and an absorbent pad. The carrier may also be referred to as a cassette or test strip. Each of these components may be combined with any other individual or group of components. In one embodiment, the carrier is nitrocellulose, which permits the immobilization of proteinaceous reagents in a capture line without prior chemical treatment. If the carrier comprises paper, for example, the immobilization of the capture binding agent may be performed by chemical coupling using, for example, CNBr, carbonyldiimidizole, or tresyl chloride. Typically, and particularly where multiple components are used, each component will be adhered to a physical support, such as, e.g., mylar, plastic, or glass. One specific embodiment of a carrier is provided in FIG. 4.

In one embodiment, the carrier comprises a dry, porous material to which a liquid sample can be applied directly or indirectly. The dry, porous material may comprise a chromatographic strip, such as a strip of nitrocellulose, which may be advantageous as proteins are capable of directly binding to nitrocellulose. Nitrocellulose is available in a variety of pore sizes, thus facilitating the selection of a carrier suitable for any particular flow requirement with minimal effort. In certain embodiments, the nitrocellulose has a pore size of at least 1 micron, at least 5 microns, or 8-12 microns. Nitrocellulose sheets are available from Schleicher and Schuell GmbH and Millipore Corporation (Billerica, Mass.).

In certain embodiments, the carrier, e.g., nitrocellulose, may be backed to increase handling strength, e.g., with a moisture impermeable material, such as mylar, a polyester sheet, plastic, or glass.

In certain embodiment, a sample is applied to the carrier via the use of a sample wick, an optional component of the carrier. The sample wick can be made from any bibulous, porous, or fibrous material capable of absorbing liquid. The porosity of the material may be unidirectional or multidirectional. Porous plastics may be used, such as, e.g., polypropylene, polyethylene, and polyvinylidene fluoride. The sample wick may also be made from paper or other cellulosic materials, such as nitrocellulose.

In certain embodiments, the carrier may comprise an optional sample pad that comprises a blocking solution, which will interact with the sample prior to the sample contacting the detection binding agent or capture binding agent to reduce non-specific binding and false positives. The sample pad is typically in direct moisture-conducting contact with the sample wick. Blocking solutions may be selected based upon the binding agent being used and are widely known in the art. For example, one blocking solution that may be used where the binding agents are antibodies is comprises bovine serum albumin (BSA). Other examples of blocking agents include, but are not limited to, casein, Blotto, trademarked blocking agents, chicken serum, BSA, fish gelatin, albumin, gelatin, Tween 20, Triton 100, glycerin, polyvinyl alcohol (PVA), polyvinyl pyrrolidone (PVP), polyethylene glycol (PEG), sodium dodecylsulfate (SDS), and sodium dodecylebenzene sulfonate (SDBS).

In one embodiment, the carrier comprises a conjugate pad, which comprises the detection binding agent, and may further comprise a secondary reagent used to detect the presence of the detection binding reagent. In one embodiment, the conjugate pad is a macroporous body wherein the applied liquid sample encounters the labeled binding agent. The use of a macroporous body is believed to facilitate the ease with which the detection binding agent binds bacteria within the sample, as compared to the situation where the detection binding agent is incorporated directly onto the dry, porous carrier. In certain embodiments, to facilitate migration of the detection binding agent, the conjugate pad has a pore size at least ten times greater than the size of the detection binding agent. In one embodiment, the conjugate pad comprises plastics material or glass fibers having an average pore size of e.g., at least 10 microns or at least 100 microns. The conjugate pad is preferably non-protein binding or readily blockable.

In certain embodiments, the conjugate pad is in direct moisture-conductive contact with the sample wick or the sample pad, and the detection zone on the carrier is spaced away from, typically downstream of, the region of contact between the carrier and the conjugate pad, as illustrated in FIG. 4.

In certain embodiments, the carriers further comprise a capture line (i.e., detection zone), which comprises the capture binding agent. The capture binding agent is immobilized at the capture line, thus facilitating the formation of a complex containing bound bacteria and detection binding agent at the capture line, where it can be detected. In one embodiment, the capture binding agent is immobilized to the capture line of the carrier (e.g., nitrocellulose) via UV cross-linking. In other embodiments, the capture agent is immobilized at the capture line using any technique available in the art and suitable for the particular material being used, including, for example, hydrophobic interactions for polyvinylidene fluoride (PVFD), the use of mixed cellulose esters (e.g., nitrate and acetate), the use of nylon (including, e.g., charge-modified or electrostatic (ionic) materials), electrostatic interactions using nitrocellulose or cellulose, and hydrophobic interactions using polyethersulfone.

In one embodiment, the capture line comprises a secondary agent, which facilitates detection of the detection binding reagent.

The devices may optionally further comprise a control line comprising a control agent capable of binding the detection binding agent. In one embodiment, wherein the detection binding agent is an antibody, the control agent is an antibody directed against immunoglobulins. For example, where the detection binding agent is a mouse monoclonal antibody, the control binding agent may be goat anti-mouse IgG1. Typically, the control line will be downstream of the capture line.

The device may also optionally comprise an absorbent pad, which is downstream from the capture line and optional control line.

The various components of the carrier are arranged, in one embodiment, as shown in FIG. 4. The spatial separation between the conjugate pad and capture line, and the flow rate characteristics of the porous materials of the carrier, can be selected to allow adequate reaction times during which the necessary specific binding can occur. Further control of these parameters may be accomplished by the addition of viscosity modifiers, e.g., sugars and modified cellulose, to the liquid sample to slow down migration.

Figure 5:
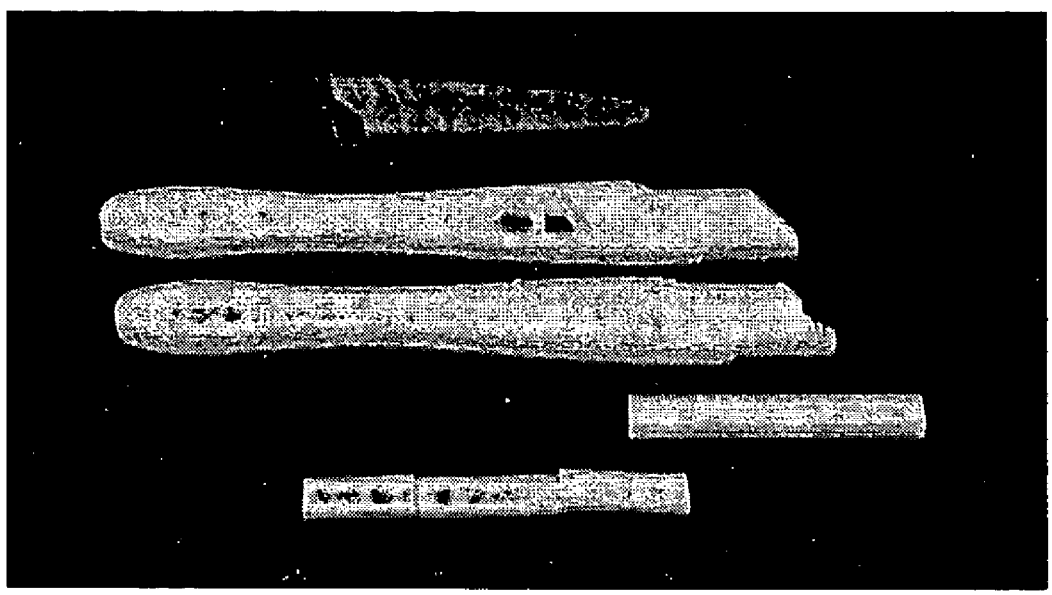
FIG. 5 is a photograph showing the major components of one embodiment of a lateral flow immunoassay cassette used for the rapid bacterial test for milk.

In certain embodiments, the carriers are contained within a moisture-impermeable casing or housing and the sample wick extends out of the housing and acts as a means for permitting the liquid sample to enter the housing. In another related embodiment, a sample may be applied to the carrier, e.g., to a sample wick or sample pad through an aperture in the housing. The housing is provided with means, e.g., appropriately placed apertures, which enable the capture line, and optional control line, to be observable from outside the housing so that the result of the detection assay can be observed. The housing may be provided with a removable cap that can protect a protruding sample wick during storage and can be placed over the sample wick while the assay is being performed. One embodiment of a device of the invention is shown in FIG. 5.

The invention further provides kits that may be used according to any of the methods described herein. Kits of the invention typically include one or more binding agents and instructions for their use. Other kits components may also be included, such as, e.g., separate capture and detection binding agents and a carrier. In certain embodiments, the invention provides kits comprising a binding agent and instructions for its use. In a particular embodiment, the binding agent is a capture binding agent. In other embodiments, the invention provides a kit comprising both a detection binding agent and a capture binding agent. In certain embodiments, a kit comprises a carrier of the invention containing these binding agents. Kits may further comprise sample dilution buffers, blocking buffers, and/or instructions for use.

EXAMPLES

Example 1

Elisa Detection of Bacteria Using an Anti-Peptidoglycan Antibody

Figure 1:
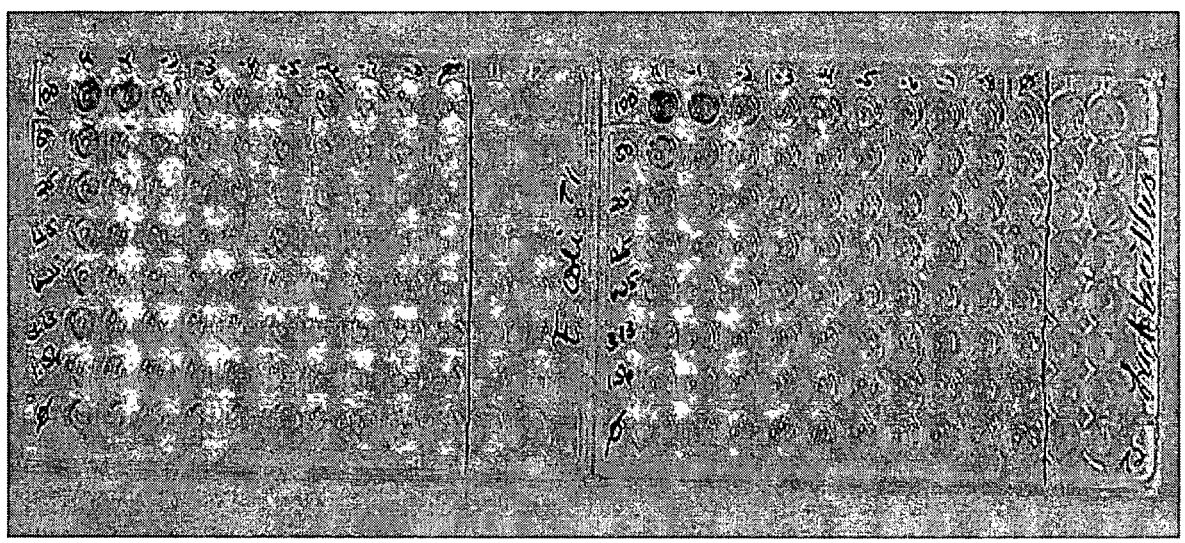

This example demonstrates that monoclonal antibodies against peptidoglycan can be used to detect the presence of gram positive and gram negative bacteria in liquid samples. FIG. 1 shows the results of an ELISA using an anti-peptidoglycan monoclonal antibody obtained from Chemicon International, (Temecula, Calif.) to detect *Lactobacillus* sp. and *E. coli* strain 392. It was also demonstrated that antibodies directed against NAG and NAM could be successfully used according to the invention.

These organisms were examined to determine if peptidoglycan antibodies detect their presence in a standard ELISA format. The procedure was carried out using a method as follows.

1. A 1 ml sample of bacteria was washed 3× in PBS and resuspended in 1 ml of PBS for a final concentration of approximately $1 \times 10^8$ cfu/ml. This was then diluted ten-fold eight times.
2. Each well received 100 ul of the appropriate dilution of bacteria. Negative control wells received an equal volume of sterile filtered PBS. The plate was covered and incubated overnight at room temperature.
3. The plate was washed 1× with PBS-Tween 20 and then 1× with PBS.
4. All wells were blocked by placing 100 ul of PBS+2% chicken serum in each and incubated for 30 min. at room temperature.
5. The plate was then washed 3× with PBS-Tween 20 and 1× with PBS.
6. Two-fold dilutions of monoclonal mouse anti-peptidolycan in PBS were prepared ranging from 100 ug/ml to 1.56 ug/ml.
7. Each well received 50 ul of the appropriate antibody dilution. Negative control wells received an equal volume of sterile filtered PBS. The plate was then incubated for 1 hour at room temperature and then an additional hour at 36 C.
8. Washed plate as in step 5.
9. Goat anti-mouse IgG(Fc) conjugated to horseradish peroxidase was diluted 1:2000 and added to all wells, 50 ul/well. The plate was incubated for 30 min. at room temperature.
10. Plates were washed again as in step 5.

11. ABTS (1 mg/ml) was added to all wells, 50 ul each, in order to produce a colored reaction. OD readings (absorbance 405 nm) were taken at 30 and 55 minutes in a Staffax Model 2100 ELISA reader fitted with the appropriate filters.

Figure 2A:
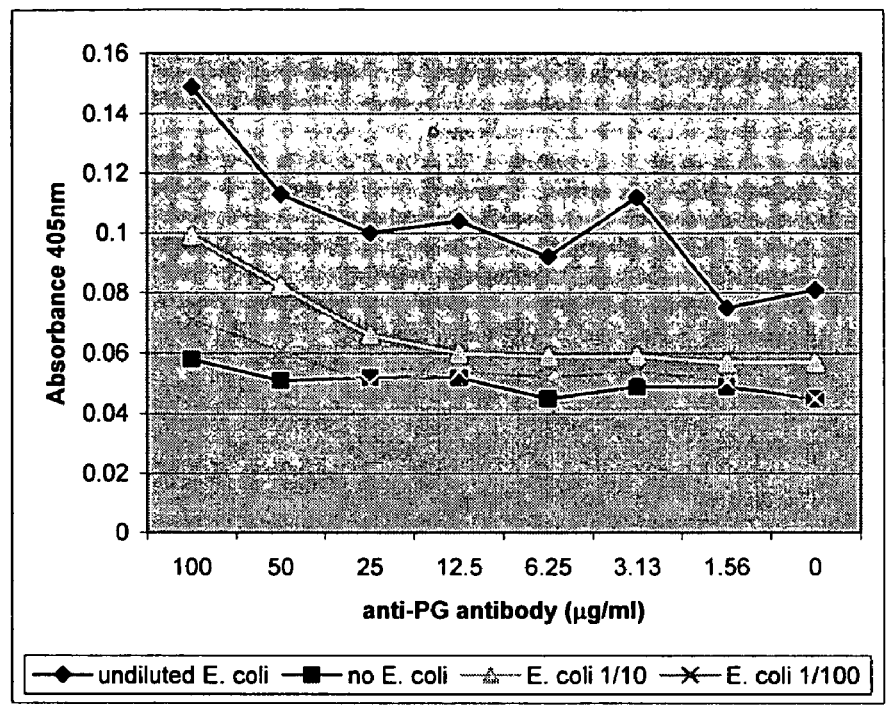
Figure 2B:
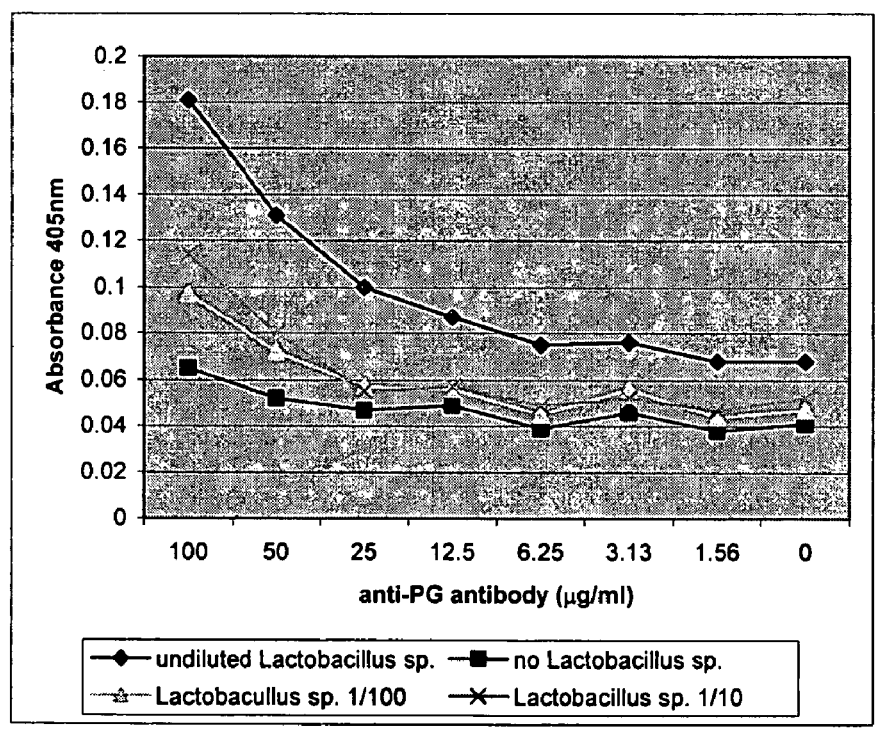

The ELISA plate results are shown in FIG. 2. An ELISA format known as a checkerboard titration was used for each type of bacteria. A 1 ml culture sample containing approximately $1 \times 10^8$ cfu was washed with three times with PBS and resuspended in 1 ml of PBS. The suspension was serially diluted ten-fold eight times. Wells in the microtiter plate received 100 ul of the various dilutions of bacteria; one dilution per column. After appropriate steps were taken, two-fold dilutions of the anti-PG antibody were added at 50 ul per well, one dilution per row. After addition of an enzyme labeled secondary antibody, ABTS was added to act as the substrate for the enzyme resulting in a color change. This color change was measured with a microtiter plate reader by recording the absorbance of each well at 405 nm.

The combination of antibody labeled conjugates required to detect $5 \times 10^3$ bacteria/ml was optimized.

These results clearly demonstrate that bacteria in liquid samples can be detected using anti-peptidoglycan antibodies and an ELISA format and, furthermore, establish that anti-peptidoglycan antibodies can be used to detect bacteria in an immunological-based assay.

Example 2

Figure 3:
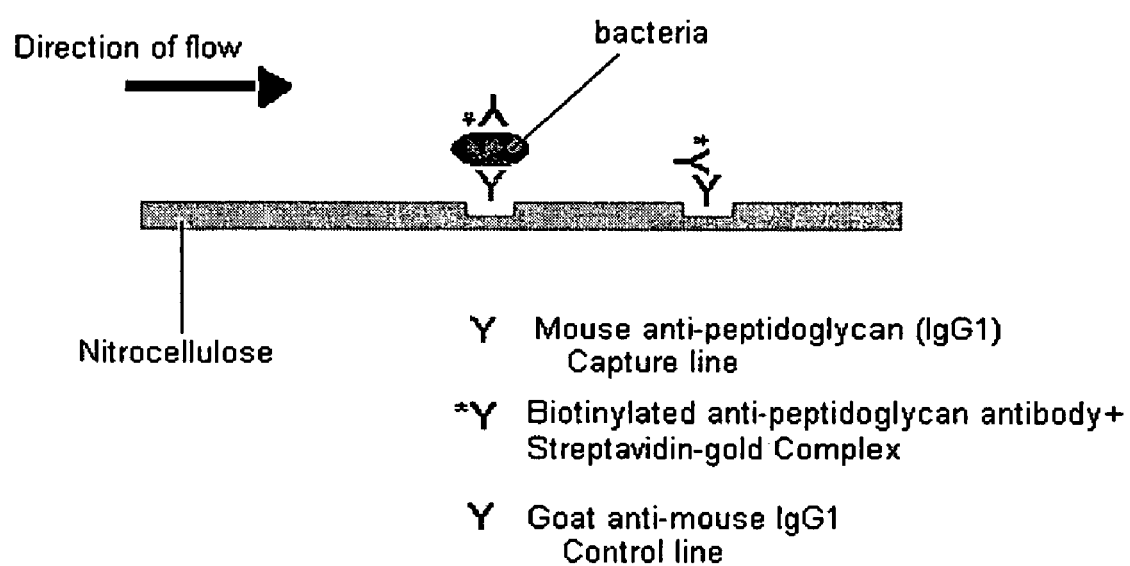
FIG. 3 is a diagram showing the basis of a capture antibody method used to determine the presence of total bacteria in raw milk with monoclonal antibodies to peptidoglycan.

Detection of Bacteria Using an Anti-Peptidoglycan Antibody in a Lateral Flow Immunological Assay This example demonstrates that bacteria can be detected in a liquid sample using a lateral flow immunological sample. Schematic diagrams of the principle of the lateral flow assay devised during this project and an exemplary lateral flow detection device are shown in FIGS. 3 and 4, respectively.

Lateral flow immunological assays were performed as depicted to optimize the relative concentrations of antibody-labeled conjugates for lateral flow detection. The purpose of these experiments was to determine the optimum concentrations of the various conjugates for detecting bacteria in the threshold range of $5 \times 10^3$ organisms/ml. Various concentrations of the capture antibody, biotin-labeled antibody and streptavidin-gold conjugate were tested in order to optimize the assay. Labeled antibodies were prepared using BiotinTag Micro-biotinylation Kit, Catalog B-Tag from Sigma Chemical Co., St Louis, Mo. This procedure was based on methods described by Jones, 1999, Millipore Corp., 2001, Chandler et al, 2000, Weiss, 1999 and Paek et al, 2000.

The standard plate count technique was used to establish concentration of bacteria detectable by the lateral flow system. The concentrations and amount of antibody and antibody conjugates were adjusted to reveal a "positive" line only when the concentration was $5 \times 10^3$ organisms/ml or above. Below this level was considered a "negative" result, since no line was visible. This provided a test that can screen liquid samples for the presence of bacteria in the range that is acceptable by dairy producers.

Once the optimal parameters were defined for concentration of antibody conjugates, a final cassette was labeled and assembled as shown in FIG. 5. This lateral flow cassette was used to detect *Lactobacillus* and *E. coli* when the bacteria were run in phosphate buffer (pH 7.0) with a sensitivity of detection of $10^3$ cfu/ml. The final design of the lateral flow carrier is shown in FIG. 6.

All of the above U.S. patents, U.S. patent application publications, U.S. patent applications, foreign patents, foreign patent applications and non-patent publications referred to in this specification and/or listed in the Application Data Sheet, including but not limited to U.S. Pat. Nos. 5,622,871 and 6,352,862, and references and patents cited therein, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A device for the detection of bacteria, comprising:
   (a) a self-contained carrier to which a liquid sample suspected of containing bacteria can be applied;
   (b) a first binding agent that is mobile in the carrier when in the moist state;
   (c) a second binding agent that is immobilized in a first region of the carrier, wherein said second binding agent is an antibody, and wherein both of the binding agents bind peptidoglycan; and
   (d) a detectable labeled secondary agent that binds the first binding agent, wherein the secondary agent comprises a detectable label and the secondary agent is not an antibody.

2. The device of claim 1, wherein the carrier comprises the following components:
   (a) a liquid sample application wick;
   (b) a conjugate pad comprising the first binding agent;
   (c) a base pad comprising the second binding agent;
   (d) a sample pad comprising a blocking solution; and
   (e) an absorbent pad.

3. The device of claim 1, further comprising a control binding agent that is immobilized in a second region of the carrier.

4. The device of claim 1, wherein the first binding agent is labeled with biotin, and the labeled secondary agent comprises streptavidin.

5. The device of claim 4, wherein the streptavidin is conjugated to colloidal gold.

6. The device of claim 1, wherein the sample is a blood product.

7. The device of claim 1, wherein the first binding agent is not an antibody.

8. The device of claim 7, where the first binding agent is a peptidoglycan recognition protein (PGRP).

9. A device for the detection of bacteria, comprising:
   (a) a self-contained carrier to which a liquid sample suspected of containing bacteria can be applied;
   (b) a first binding agent that is mobile in the carrier when in the moist state, wherein the first binding agent is not an antibody;
   (c) a second binding agent that is immobilized in a first region of the carrier, wherein said second binding agent is an antibody, and wherein both of the binding agents bind peptidoglycan; and
   (d) a detectable labeled secondary agent that binds the first binding agent, wherein the secondary agent comprises a detectable label and the secondary agent is not an antibody.

10. The device of claim 9, where the first binding agent is a peptidoglycan recognition protein (PGRP).

* * * * *